(12) United States Patent
Dugan et al.

(10) Patent No.: US 7,545,280 B2
(45) Date of Patent: Jun. 9, 2009

(54) SECURITY SCREENING AND SUPPORT SYSTEM

(75) Inventors: Regina E. Dugan, Rockville, MD (US); Thomas Emory McVeigh, Shenandoah Junction, WV (US); Jacek Kotowicz, Fairfax, VA (US)

(73) Assignee: Redxdefense, LLC, Rockville, MD (US)

( * ) Notice: Subject to any disclaimer, the term of this patent is extended or adjusted under 35 U.S.C. 154(b) by 441 days.

(21) Appl. No.: 11/418,193

(22) Filed: May 5, 2006

(65) Prior Publication Data

US 2007/0182552 A1 Aug. 9, 2007

Related U.S. Application Data

(60) Provisional application No. 60/678,195, filed on May 6, 2005, provisional application No. 60/702,621, filed on Jul. 27, 2005.

(51) Int. Cl.
*G08B 23/00* (2006.01)
(52) U.S. Cl. .............. 340/573.1; 340/522; 340/540; 340/521; 340/5.3
(58) Field of Classification Search ............ 340/522, 340/573.1, 552, 540, 5.12, 5.3, 5.32, 5.7, 340/521, 541; 700/226, 229, 213; 73/23.2, 73/28.1; 378/63
See application file for complete search history.

(56) References Cited

U.S. PATENT DOCUMENTS

| | | | |
|---|---|---|---|
| 5,483,601 A | 1/1996 | Faulkner | |
| 5,566,327 A | 10/1996 | Sehr | |
| 5,571,976 A | 11/1996 | Drolet | |
| 5,741,984 A | 4/1998 | Danylewych-May et al. | |
| 5,818,047 A | 10/1998 | Chaney et al. | |
| 6,073,499 A | 6/2000 | Settles | |
| 6,078,928 A | 6/2000 | Schnase et al. | |
| 6,424,264 B1 | 7/2002 | Giraldin et al. | |
| 6,529,786 B1 | 3/2003 | Sim | |
| 6,610,977 B2 | 8/2003 | Megerle | |
| 6,721,391 B2* | 4/2004 | McClelland et al. | .......... 378/57 |
| 6,899,540 B1* | 5/2005 | Neiderman et al. | ......... 434/219 |
| 6,914,668 B2 | 7/2005 | Brestel et al. | |
| 6,937,147 B2 | 8/2005 | Dilbeck et al. | |
| 6,950,536 B2* | 9/2005 | Houvener | .................. 382/116 |
| 6,952,163 B2 | 10/2005 | Huey et al. | |
| 6,976,032 B1 | 12/2005 | Hull et al. | |
| 7,136,513 B2 | 11/2006 | Waehner et al. | |
| 2002/0070863 A1 | 6/2002 | Brooking | |
| 2002/0070865 A1 | 6/2002 | Lancos et al. | |
| 2002/0082897 A1 | 6/2002 | Menelly et al. | |
| 2003/0128100 A1 | 7/2003 | Burkhardt et al. | |
| 2003/0130035 A1 | 7/2003 | Kanarat | |

(Continued)

*Primary Examiner*—Anh V La
(74) *Attorney, Agent, or Firm*—Diederiks & Whitelaw, PLC

(57) ABSTRACT

A personnel security screening and control system includes a screening center having a threat screening system incorporating a sample collector and a sample analyzer. The sample collector obtains a threat sample from the subject which is subsequently analyzed by the sample analyzer to determine whether the individual represents a potential threat. The overall system also incorporates a demographic screening system including a demographic collector and a demographic analyzer. The demographic collector obtains a demographic indicator which is subsequently analyzed to determine a particular demographic of the subject. The screening center provides an interactive system for determining whether a subject has encountered or handled a substance that may pose a potential threat, e.g., explosives, and also presents targeting advertising or other information to the subject.

20 Claims, 8 Drawing Sheets

U.S. PATENT DOCUMENTS

| | | |
|---|---|---|
| 2003/0142853 A1 | 7/2003 | Waehner et al. |
| 2004/0169589 A1 | 9/2004 | Lea et al. |
| 2004/0230437 A1 | 11/2004 | Havrilak, Jr. |
| 2004/0252024 A1 | 12/2004 | Huey et al. |
| 2005/0024204 A1 | 2/2005 | Germaine et al. |
| 2005/0043897 A1 | 2/2005 | Meyer |
| 2005/0045710 A1 | 3/2005 | Burke et al. |
| 2005/0057354 A1 | 3/2005 | Jenkins et al. |
| 2005/0074147 A1 | 4/2005 | Smith et al. |
| 2005/0137890 A1 | 6/2005 | Bhatt et al. |
| 2005/0251398 A1 | 11/2005 | Zanovitch et al. |
| 2005/0256724 A1 | 11/2005 | Rasin et al. |
| 2005/0264416 A1 | 12/2005 | Maurer |
| 2005/0270158 A1 | 12/2005 | Corbett, Jr. |
| 2005/0288937 A1 | 12/2005 | Verdiramo |
| 2006/0000903 A1 | 1/2006 | Barry et al. |
| 2006/0015503 A1 | 1/2006 | Simons et al. |
| 2006/0017541 A1 | 1/2006 | Nguyen |

\* cited by examiner

FIG. 7

| SUBSECTOR | NEEDS ATTENTION | STATE | LAST CHANGE | DAYS SINCE CHANGE | END DATE | PROCEDURE | REASON FOR CHANGE |
|---|---|---|---|---|---|---|---|
| TRANSPORT | O | ELEVATED | 06/11/05 | 2 | 06/28/05 | 11,44,01 | DHS ADVISORY |
| ENTRANCES | O | ELEVATED | 06/11/05 | 3 | 06/28/05 | 02,34 | THREAT ENDED |
| UTILITIES | O | SEVERE | 06/11/05 | 1 | 06/28/05 | 11,22,33 | REQUEST FROM PARK |

FIG. 8

| PROCEDURE | STATUS | DATE DUE | REMAINING | CONTACT | VENUE COMMENTS |
|---|---|---|---|---|---|
| 11 | O | 06/11/05 | 0 | JOHN WHITE<br>804-555-1212<br>JWHITE@FUN.COM | COMPLETE |
| 22 | O | 06/11/05 | 0 | JOHN WHITE<br>804-555-1212<br>JWHITE@FUN.COM | COMPLETE |
| 33 | O | 06/11/05 | 0 | JOHN WHITE<br>804-555-1212<br>JWHITE@FUN.COM | COMPLETE |
| 44 | O | 06/11/05 | -3 | JOHN WHITE<br>804-555-1212<br>JWHITE@FUN.COM | COMPLETE |
| 55 | O | 06/08/05 | 0 | JOHN WHITE<br>804-555-1212<br>JWHITE@FUN.COM | WAITING FOR CONTRACTOR |
| 66 | O | 06/11/05 | 0 | JOHN WHITE<br>804-555-1212<br>JWHITE@FUN.COM | COMPLETE |
| TEST ALERT | O | 06/14/05 | 0 | JOHN WHITE<br>804-555-1212<br>JWHITE@FUN.COM | COMPLETE |

SECURITY SCREENING AND SUPPORT SYSTEM

CROSS REFERENCE TO RELATED APPLICATIONS

The present invention claims the benefit of U.S. Provisional Patent Application Ser. No. 60/678,195 entitled "Personnel Screening and Security System With Dynamic, Individualized Subject Interface" filed May 6, 2005 and U.S. Provisional Patent Application Ser. No. 60/702,621 entitled "Kiosk/Security Decision Support System" filed Jul. 27, 2005.

BACKGROUND OF THE INVENTION

1. Field of the Invention

The present invention pertains to the art of security systems and, more specifically, to a personnel security screening and response control system for use in providing security screening in a wide range of venues, particularly where user attention to increased security measures is not desired.

2. Discussion of the Prior Art

Since Sep. 11, 2001, protection against terrorist threats has become a national priority. This priority extends from the protection of government facilities inside the U.S. and abroad to the protection of private businesses and venues. Various types of threats have been postulated, including attacks using explosives, chemical and/or biological agents, as well as nuclear and radiological agents (dirty bombs). The diversity of these threats has created complex security challenges for national, state, and local governments, the transportation industry, private businesses, and even individuals. Total expenditures related to Homeland Security topped $100B in 2003 and billions have been allocated in Federal, Supplemental Appropriations and State/Local spending. Increasingly, U.S. businesses are devoting more revenue to security systems, with total expenditures reaching tens of billions of dollars. Growth in the homeland security industry is expected to be vigorous over the next decade. Motivated by the wide diversity of potential threats and by the inadequacy of currently available systems, government investments in research and development are on the rise.

Of the various threats postulated, explosives remain the number one choice of most terrorists. Indeed, many experts have noted that, in the case of terrorist activity, compelling statistical evidence exists that bombs are a primary threat. Additional studies have shown that most deaths and injuries occur in locations where security screening is not typically present, highlighting the importance of protecting high-value locations lacking a security screening system. As security systems in government facilities improve, businesses and other non-government venues become increasingly attractive targets, with public safety, security and the economic health of businesses being held at risk.

Experience in aviation security has shown that employing moderately effective portal screening to screen 100% of personnel increases operational risk to would-be attackers and is thus a significant deterrent. Indeed, most of the security systems currently available were developed in response to regulatory pressures pertaining to aviation security. However, since the use of such systems by individuals was mandated, to date the development of these systems has been focused on security sensors themselves, with little attention being given to user interactions or ease of use. Prior methods of providing for personnel screening and security involve costly, large fixed base, and low throughput systems. Indeed, these systems are most often associated with long lines, user frustration, false alarms, and irritating delays for the personnel being screened.

The above described systems were not designed with the needs of businesses in mind, especially with regard to providing security in a manner that is consistent with their objectives and image. Furthermore, existing interfaces for security and personnel screening are not readily adaptable to different individuals or to changes in security sensing technology. In the case of explosives screening, current systems often cost more than $1M per portal for systems that detect bulk explosives, and tens of thousands of dollars per portal for systems that detect trace explosives. Moreover, installation and annual maintenance costs often times exceed the original price of the system. In the case of trace explosive detection, currently deployed systems were developed primarily for use by analytical chemists in laboratories and thereafter adapted for use in the field. Current trace explosive detection systems suffer from very long clearance times following a positive detection (15-30 minutes), have exceedingly high false alarm rates and require extensive training to ensure proper use and maintenance.

Trace explosive detection systems are based on wide scientific evidence which indicates that handling of explosives leaves trace residues on hands, clothes, and other materials. These residues are highly concentrated and difficult to eradicate. Actually, the Federal Aviation Administration relies on this principle as a basis for their trace explosive detection program. Indeed, contamination is expected to be so extensive and difficult to eliminate that currently installed trace explosive detection systems depend on secondary contamination transferred from the hands and clothes of individuals to their baggage. Baggage is sampled for trace explosives, and samples obtained are presented to detection systems for analysis.

While currently deployed trace detection systems operating on this principle have high sensitivity, false alarm rates and low throughput require that only a small fraction of personnel be screened. As a result, probability of detection is quite low. Moreover, most businesses and unregulated industries are not at risk from the very small quantities of explosives that are a threat to aircraft and thus do not require the explosive detection capabilities needed by aviation security. A better operational point for such cases would be the ability to screen 100% or nearly 100% of individuals using a high throughput, customized system, with fewer false alarms. Raising the percentage of individuals screened will increase the overall probability of detection, as well as the level of deterrence.

Further, it is known that explosive contamination can vary widely over small spatial distances. Evidence indicates that trace residue levels can change as much as 10,000 fold over distances as short as a few centimeters. Currently available trace explosive detection systems sample only from limited spatial areas, with swipes of these areas provided to a fixed base system. Thus, there is a need to improve upon the spatial sample and analysis of explosive contamination.

As described above, currently available screening systems suffer from many disadvantages such as high cost, low throughput, high false alarm rates, operational complexity, high maintenance and training requirements, poor spatial sampling and the like. In addition, as the currently available systems are focused on individual security sensor systems rather than the user interface, these systems are not easily upgraded with new technological solutions and/or designed to create a positive experience for users. These limitations have created a significant barrier to the use of such systems when convenience of use is paramount to meeting the combined needs of security and access to businesses in particular. More specifically, the security of large venues and transportation hubs has become a distinct challenge for businesses, state and local governments, as well as the federal government in the United States and abroad.

Improving security requires the formulation of effective tactics, techniques, and procedures which are tailored to the particular threat level, the location and available assets, as well as the consistent application of these approaches to reduce vulnerabilities. Moreover, as attacks are rare events, it is critical that a system exist for promulgating and exercising security procedures, as well as for measuring improvements in the response to real or simulated events. Taken together, such a system would permit an entity to establish best practices and achieve a state of readiness for individual venues, as well as across an entire company. Current approaches to security are ad hoc and do not utilize sophisticated decision support aids, modem software and communication tools, authentication procedures, or audit trail creation.

As such, there is a need to improve the interface and experience of personnel screening processes. More specifically, there exists a need for a personnel screening and security system that collects subject data through the use of a user friendly, even entertaining, interface. In addition, there is a need for a support system that integrates multiple security interfaces which are positioned in multiple locations. Moreover, there is a need for a security screening and support system that meets the needs of unregulated industries and businesses wishing to improve security in a manner that is consistent with current business objectives, desired user interactions, and a changing technological landscape.

SUMMARY OF THE INVENTION

The present invention is directed to a personnel security screening and support system including a screening center having a main housing within which is arranged a threat screening system and a demographic screening system. The screening center establishes an interactive system for determining the potential threat of a subject, e.g., whether a subject has recently encountered or handled an explosive substance that may pose a potential threat. In one preferred embodiment, the screening center also determines a particular demographic of the subject in order to present targeted advertising or other information to ensure that the subject's interaction with the screening system is pleasant.

In accordance with the invention, the threat screening system includes a threat data collector and a data analyzer. At this point, it should be noted that the data analyzer employed would depend on the particular threat data collected which can take various forms in accordance with the invention. That is, the threat data collector includes a sample collector which obtains one or more assessment samples from an individual, either physically or passively, with the sample(s) being processed through the data analyzer to establish a threat potential for that particular individual. Where explosive-based threats are of particular concern, the threat sample collector preferably obtains a trace residue sample from the subject which is subsequently analyzed by a sample analyzer to determine whether the trace residue sample contains a threat residue. For instance, in accordance with one preferred embodiment of the invention, a trace residue sample is obtained from a subject's hand. More specifically, the subject's hand is placed a sample collecting sheet onto which any foreign particles or trace residue would be transferred. The sheet is then shifted to the sample analyzer which determines whether the trace residue contains any threat residue, such as explosive particles, chemicals or the like. The particular form of analysis can also vary depending on the particular threat form being targeted. In the case of the explosive residual analysis, a preferred embodiment exposes the sample to various reagents and UV light in order to establish a threat signature. At the same time threat data is collected from the subject, demographic information is also preferably obtained.

In further accordance with the invention, the demographic screening system includes a demographic collector and a demographic analyzer. The demographic collector obtains a demographic indicator or attribute information from the subject. In accordance with a preferred embodiment of the invention referenced above, when the subject's hand contacts the sample collecting sheet, a hand size or other features of the hand are determined. The demographic analyzer compares the collected hand feature(s) with stored demographic information to determine a particular demographic of the subject. In addition, other physical attributes, such as height, weight, and facial attributes, could also be employed to determine the particular demographic.

In accordance with one preferred embodiment of the invention, once a subject is analyzed from a threat standpoint, and the demographic indicator is analyzed for the particular demographic of the subject, the screening center preferably issues the subject an article, in the form of a keepsake. Unbeknownst to the subject, the keepsake, which includes a picture of the subject taken at the screening center, is also preferably provided with a visual indicator associated with the threat signature, e.g., an indication of whether the trace residue sample contained a threat residue, as well as advertising targeted to the subject's particular demographic. That is, in accordance with this preferred form of the invention, the keepsake contains a hidden indicator, such as a code or icon, embedded in the keepsake and visually identifiable to security personnel, relating to whether the subject is determined to be a potential threat. In addition to issuing the keepsake at the screening center, other security measures are taken, particularly the dispatching of security personnel. Certainly, other security procedure options can be employed, such as refusing to issue the keepsake and detaining the subject.

As indicated above, the security screening centers of the invention can be employed in a wide range of environments, but preferably venues where prominent screening procedures are not welcome. For instance, the invention has particular application for use in screening visitors and guests wishing to enter amusement parts, concerts, race tracks, athletic events and the like. In accordance with the most preferred form of the invention, a group, pod or cluster of screening centers is arranged at a distance from each entry point of a particular venue. Members of the public wishing to enter the venue must first interact with the screening center, be screened and receive a keepsake. Upon reaching the venue, the subject presents both a pre-purchased ticket and the keepsake to a security screener, or an integrated ticket/keepsake. In addition to handling the ticket, the security screener scans the keepsake for the embedded code and, if the embedded code indicates that the subject is not a threat, the subject is permitted to enter the venue. If, on the other hand, the embedded code indicates that the subject may constitute a threat, the subject is taken aside for additional screening. In accordance with another embodiment, any individual not passing the screening analysis is flagged at a remote control station in communication with each of the screening centers and appropriate security measures are taken to assure that the individual does not even reach a venue entry point.

An aspect of the present invention is particularly directed to a security screening and support system for a venue having a plurality of access points. The system preferably includes a plurality of screening centers connected to a central control. The plurality or screening centers are strategically placed in relation to the plurality of access points of the venue. Preferably, multiple screening centers are arranged in pods or clusters which are positioned remote from each of the plurality of access points, such as in parking lots or other areas leading to a main venue site. In general, the exact positioning and number of screening centers can vary depending on at least the particular site configuration, logistics and the volume of people likely to enter the venue for an event. In any case, the screening centers collect samples, either through direct physical contact or passive sensing/transmission arrangements, from subjects looking to enter the venue. The samples are then screened for a threat. If a subject tests positive, an alert status is sent to the central control and a response is formulated.

In further accordance with the invention, the central control integrates each of the plurality of screening centers at a single location. The central control enables security personnel to view a target subject at any one of the plurality of screening centers, provide an alert indicating that a particular subject has a positive test result, and either enact an appropriate response dependent upon a preset threat level or alter the threat level and response based on the results. In addition to providing a command center in connection with responding to an actual threat, a test alert can be run from the central control, while a monitoring responses to the test alert. Furthermore, the central control allows security personnel to evaluate procedures for addressing various threat conditions and log alert information from each of the plurality of screening centers to establish an audit trail.

Additional objects, features and advantages of the present invention will become more readily apparent from the following detailed description of preferred embodiments when taken in conjunction with the drawings wherein like reference numerals refer to corresponding parts in the several views.

BRIEF DESCRIPTION OF THE DRAWINGS

FIG. 7 is a central control display illustrating an alert status for portions of the venue of FIG. 5; and FIG. 8 is a central control display illustrating the alert procedure status for portions of the venue of FIG. 5.

DETAILED DESCRIPTION OF THE PREFERRED EMBODIMENTS

Figure 1:
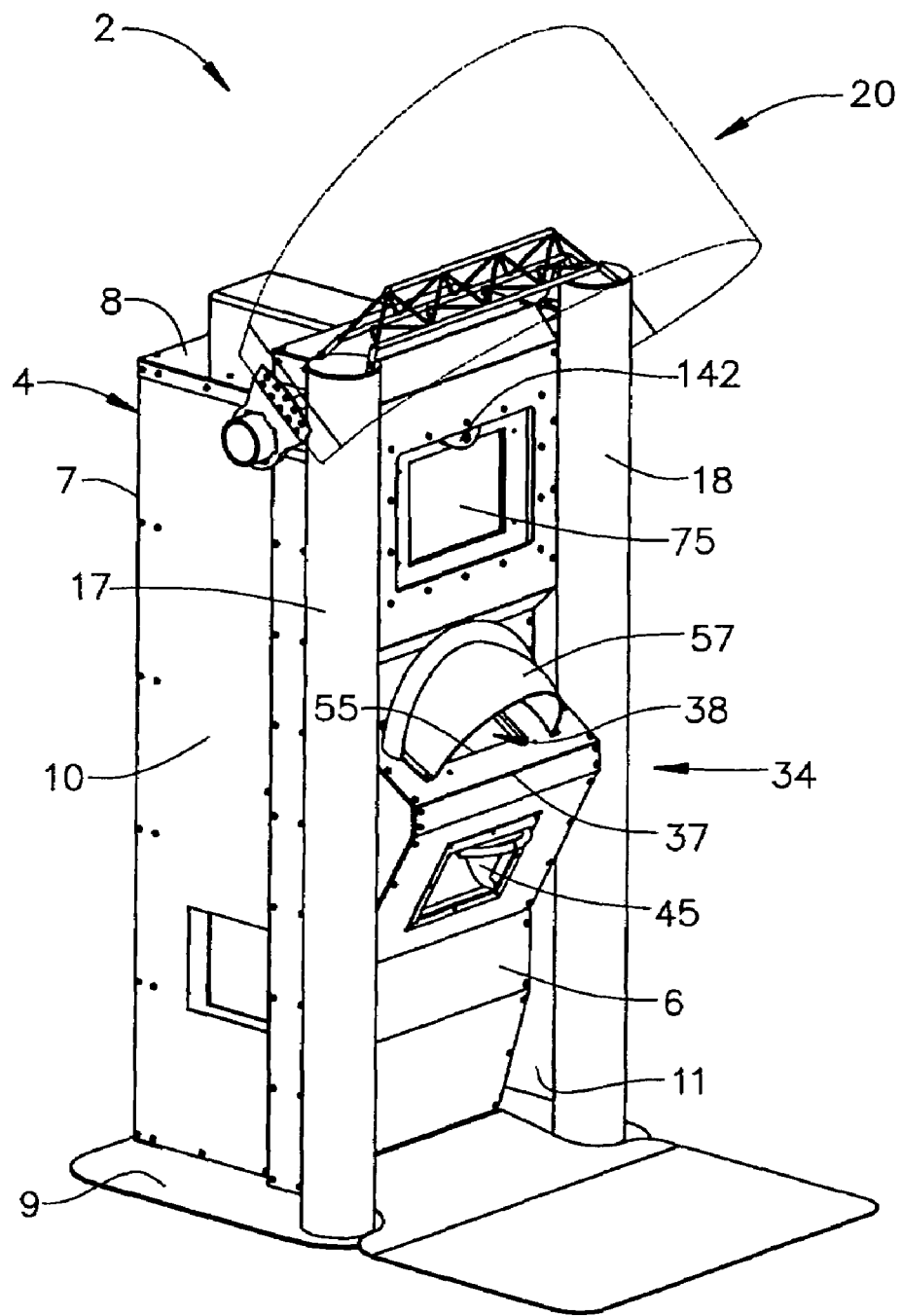
FIG. 1 is a perspective view of a screening center constructed in accordance with the present invention.
Figure 2:
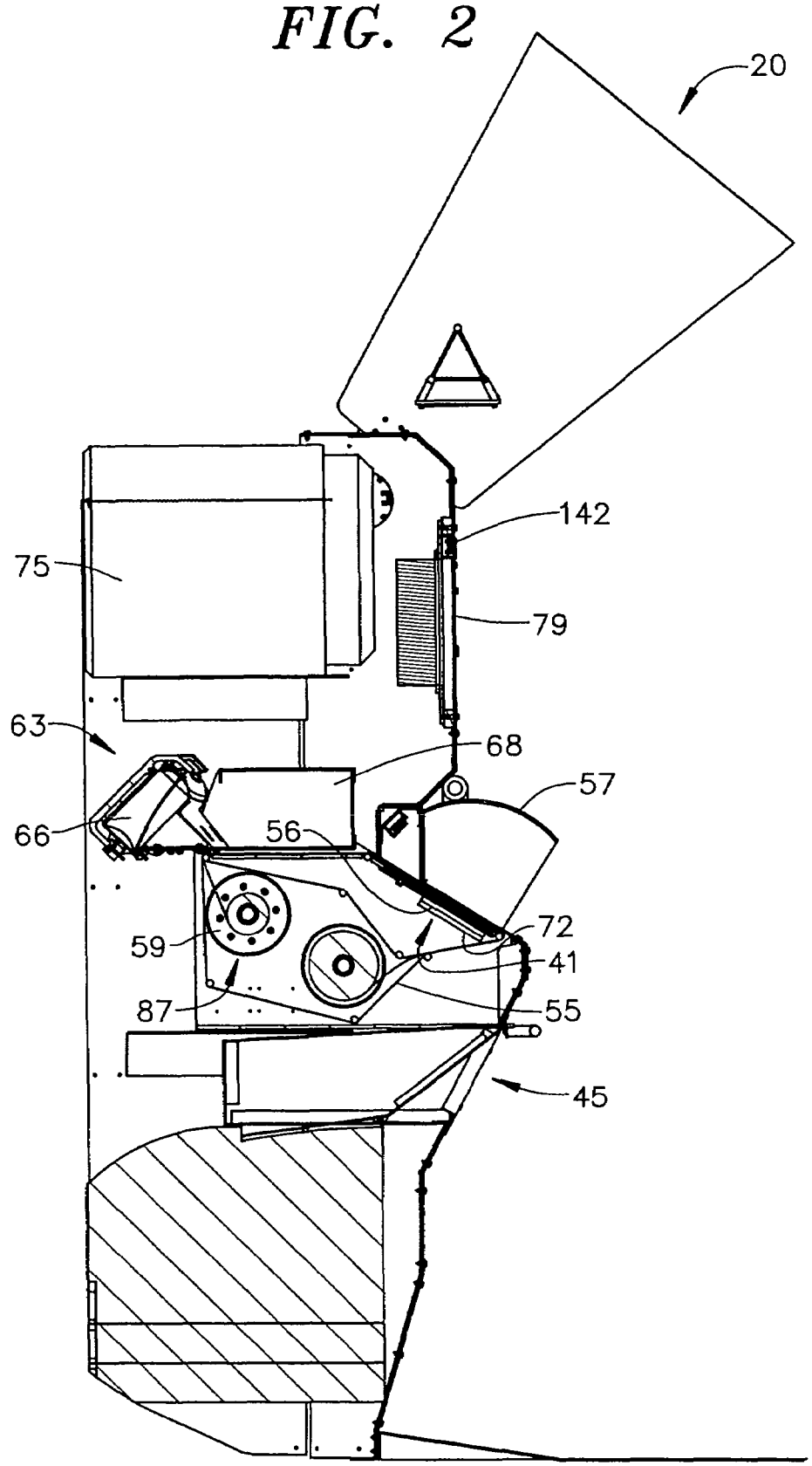
FIG. 2 is a cut-away side view of the screening center of FIG. 1.

As will become more fully event below, the present invention can take various forms and scan for various potential threats. However, initial reference to FIGS. 1 and 2 in describing a preferred form of the invention wherein a personnel screening center or kiosk employed in the security screening and support system of the present invention is generally indicated at 2. Screening center 2 includes a main housing 4 provided with a front wall 6, a rear wall 7, a top wall 8, a bottom wall or base 9 and opposing side walls 10 and 11. In addition, screening center 2 is provided with various accessories that enable screening center 2 to blend in or match a particular venue or location. For example, in the embodiment shown, screening center 2 is shown with a pair of columns 17 and 18, as well as a shield 20, which represents a configuration employed in connection with an auto racing venue. At this point, it should be understood that screening center 2 can take various forms within the scope of the invention. Preferably, each screening center 2 is designed to blend into the environment of the particular venue in which it is employed.

In any event, screening center 2 includes a collecting portion 34 arranged within a housing 37 that retrieves trace residue samples and certain demographic samples from a subject. As such, collecting portion 34 includes a residue sample collector 38 and a demographic sample collector 41, as well as an output portion 45 which, as will be described more fully below, outputs or issues an article to the subject upon completion of a screening process.

In accordance with the invention, residue sample collector 38 includes a sample collecting sheet 55 positioned upon a palm pad 56 below a cowl 57. Sample collecting sheet 55 is provided on a continuous roll 59 that enables screening center 2 to provide a clean sheet for each subject. In any case, sample collecting sheet 55 includes a slightly adhesive or tacky surface that attracts trace residue from the subject. Once a trace residue sample has been collected from the subject, sample collecting sheet 55 is moved to a sample analyzer 63. Upon reaching sample analyzer 63, chemical reagents stored within a chemical reagent dispenser 66 are sprayed onto sample collecting sheet 55 and a test for a threat residue by an analyzing portion 68 of sample analyzer 63 is performed. As will be discussed more fully below, palm pad 56 preferably includes a pressure pad or pad sensor 72 operatively coupled to analyzing portion 68 in connection with obtaining a good sample, as well as a demographic control center 75 for determining a particular demographic of the test subject.

Figure 3:
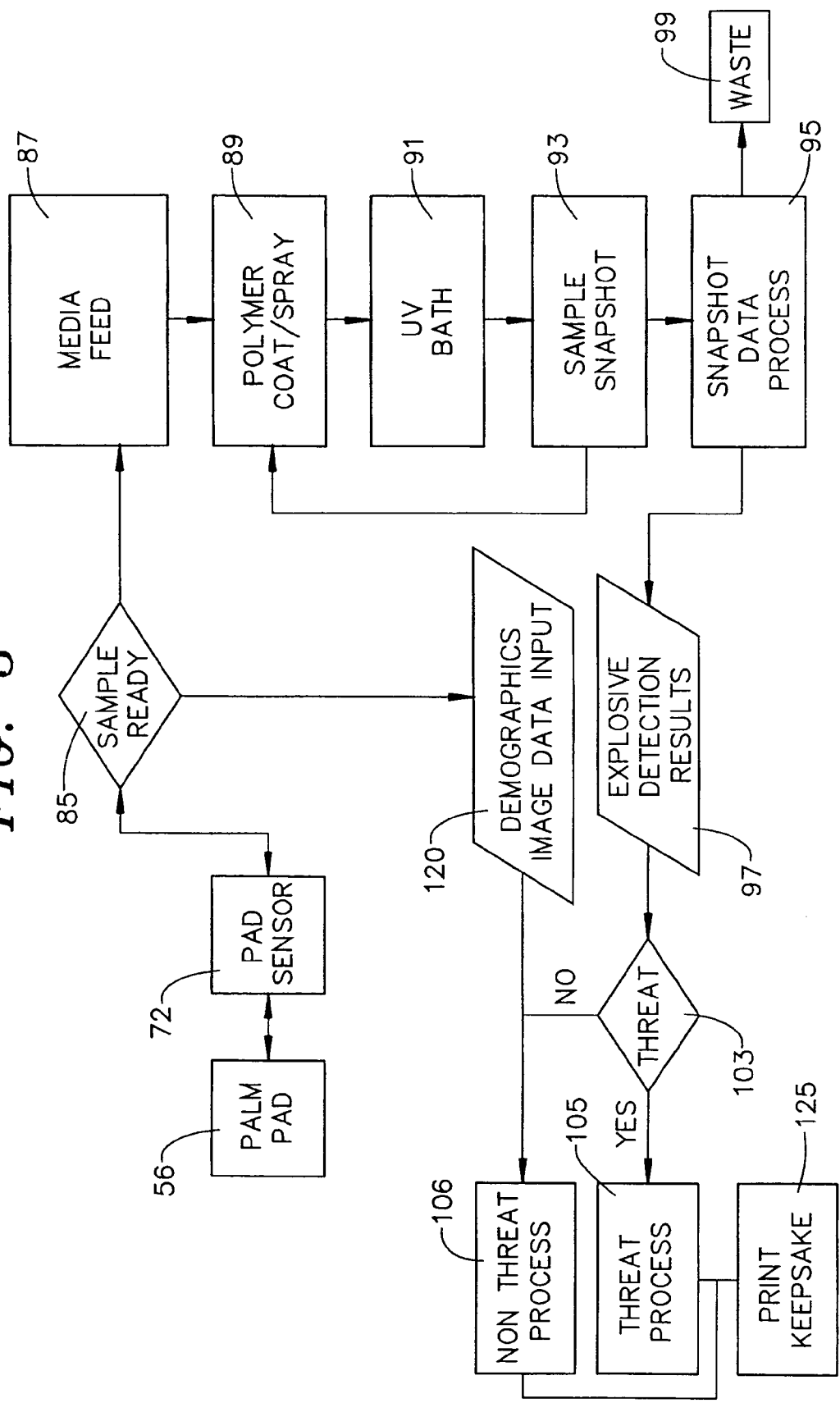
FIG. 3 is a flow chart depicting a preferred sample collection and analysis process employed in connection with the present invention.

Reference will now be made to FIG. 3 in describing a preferred screening and analyzing sequence designed to occur at screening center 2. Upon approaching screening center 2, a subject places, for example, his/her hand upon sample collecting sheet 55 and against palm pad 56, thereby triggering pad sensor 72. If insufficient pressure is applied to palm pad 56, a warning or further instructions are presented to the subject on a display 79, such as requesting that additional pressure be applied. In connection with the embodiment shown, a silhouette or outline of a hand, which may or may not correspond to the hand size of, in the case of the exemplary race car venue, the hand of a famous race car driver associated with the particular event for an amusing size comparison for the user, is provided at residue sample collector 38 for properly positioning the subject's hand. The inclusion of pad sensor 72 assures that the subject provides a sufficient pressure to obtain a proper sample as indicated in step 85. Thereafter, a media feed system 87 transfers sample collecting sheet 55 to reagent dispenser 66 where, as shown in step 89, a polymer coating or spray is applied. Once coated, sample collecting sheet 55 is passed under a UV bath 91 of analyzing portion 68 to obtain a sample image 93. If necessary, the process of coating and bathing sample collecting sheet 55 can be repeated a number of times with different chemicals to scan for wider ranges of explosives so as to obtain an accurate and comprehensive result. In any case, once one or more sample images 93 are obtained, the images 93 are analyzed for a threat residue at 95. Although various known explosive detection analysis arrangements can be employed, including spectroscopic systems, it is preferred to simply coat the sample with one or more chemicals which will chemically react with any existing explosive residue such that the residue will be readily identifiable upon be exposed to the UV light at 91. This particular technique is preferred because it is known to be accurate, involves simple and robust hardware, yet is cost effective. In any case, such explosive detection techniques are known in the art and do not form a particular aspect of the invention such that they will not be discussed further herein.

Upon completion of the analysis, an explosive detection result 97 is obtained, after which sample collecting sheet 55 is moved to a waste or collection zone in step 99. If analyzing portion 68 detects the presence of a threat in step 103, screening center 2 is caused to initiate a threat sequence, which will be discussed more fully below, in step 105 and if no threat residue is detected, screening center 2 follows a non-threat process as indicated at step 106.

At the same time sample collecting sheet 55 is being analyzed for threat residue, demographic control 75 preferably analyzes and determines a particular demographic of the subject in step 120. In the embodiment shown, demographic control 75 employs, for example, hand size, hand pressure or other feature(s), in order to determine a particular demographic of the test subject. Upon determining a particular demographic of the test subject, advertising targeted to the particular demographic is collated as part of non threat process 106. Thereafter, information is printed in step 125 onto an article or keepsake 130 which is dispensed at output portion 45. At this point, it should be noted that keepsake 130 is preferably provided with various information and data which the subject will likely wish to obtain, as well as information and data of potential interest to security personnel. For instance, keepsake 130 is preferably provided with event memorabilia on the particular event which the subject has paid to witness. This memorabilia can take various forms, such as pictures, stats, and other event information. In addition, keepsake 130 is preferably provided with targeted advertising. Furthermore, keepsake 130 contains a visual indicator on the analysis done of the sample residue.

Figure 4:
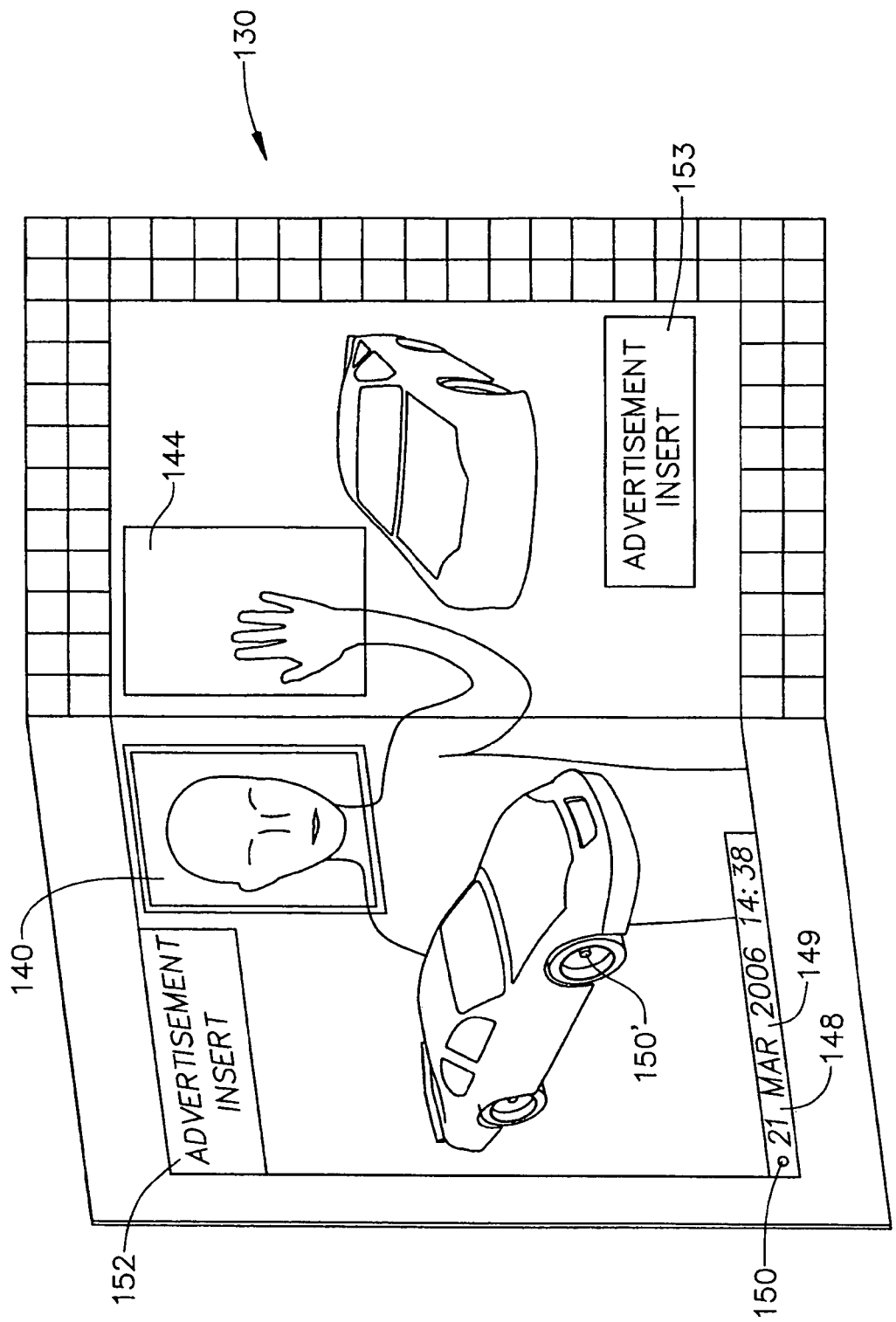
FIG. 4 depicts an article or keepsake issued from the screening center following completion of the sample collection and analysis process of FIG. 3.

FIG. 4 schematically illustrates the inside of one keepsake 130 produced in accordance with the invention. As shown, keepsake 130 includes a first photo portion 140 having a still photograph of a facial portion of the subject obtained via a camera 142 positioned on screening center 2. In addition to first photo portion 140, keepsake 130 includes a second photo portion 144 illustrating a hand portion of the subject obtained during the screening process. In the embodiment shown, keepsake 130 is depicted in connection with a car race venue such that the subject and the subject's hand is shown slowing a car into, for example, pit row, so as to provide the subject with a level of amusement following the screening process. More importantly, however, keepsake 130 includes a threat indicating portion 148 that includes a time/date indicator 149 and a threat indicator 150. Threat indicator 150 can be presented in various colors and/or forms in order to inform security personnel that the subject has or has not tested positive for a threat residue. Of course, a wide range of threat indicators could be employed such as, for example, providing a particular color on an automobile hub 150' or the like. In general, it is simply desired to provide some type of marking or identifying indicia on keepsake 130 which would provide a readily visual indication to any security personnel looking at keepsake 130 whether the particular individual matches the picture in first photo portion 140 and if the individual tested positive for explosive detection. Finally, keepsake 130 is shown to include a plurality of advertisement portions 152 and 153 that present advertisements targeted to the particular demographic of the subject ascertained during the sample collection process. In addition to providing advertisements on keepsake 130, screening center 2 can provide advertisements, news, event information or the like during the screening process on display 79 to further enhance the subject's interaction and enjoyment with the screening process. Of course, presenting this information can actually be used in connection with financing the overall cost and maintenance of the overall system.

At this point, it should be realized that each subject tested by screening center 2 receives a dedicated keepsake 130 due to the individual picture in first photo portion 140 and the hand print. It is an aspect of the invention that a requisite keepsake 130 be required, along with a ticket, invitation or the like, for each individual attempting to enter the particular venue. Therefore, each keepsake 130 is obtained outside the venue and, preferably, a substantial distance from an entry point to the venue, such as in or adjacent a parking lot for the event. Regardless, each subject wishing to enter the venue must present his/her keepsake 130 to security personnel who matches the picture to the individual and scans keepsake 130 for threat indicator 150.

Figure 5:
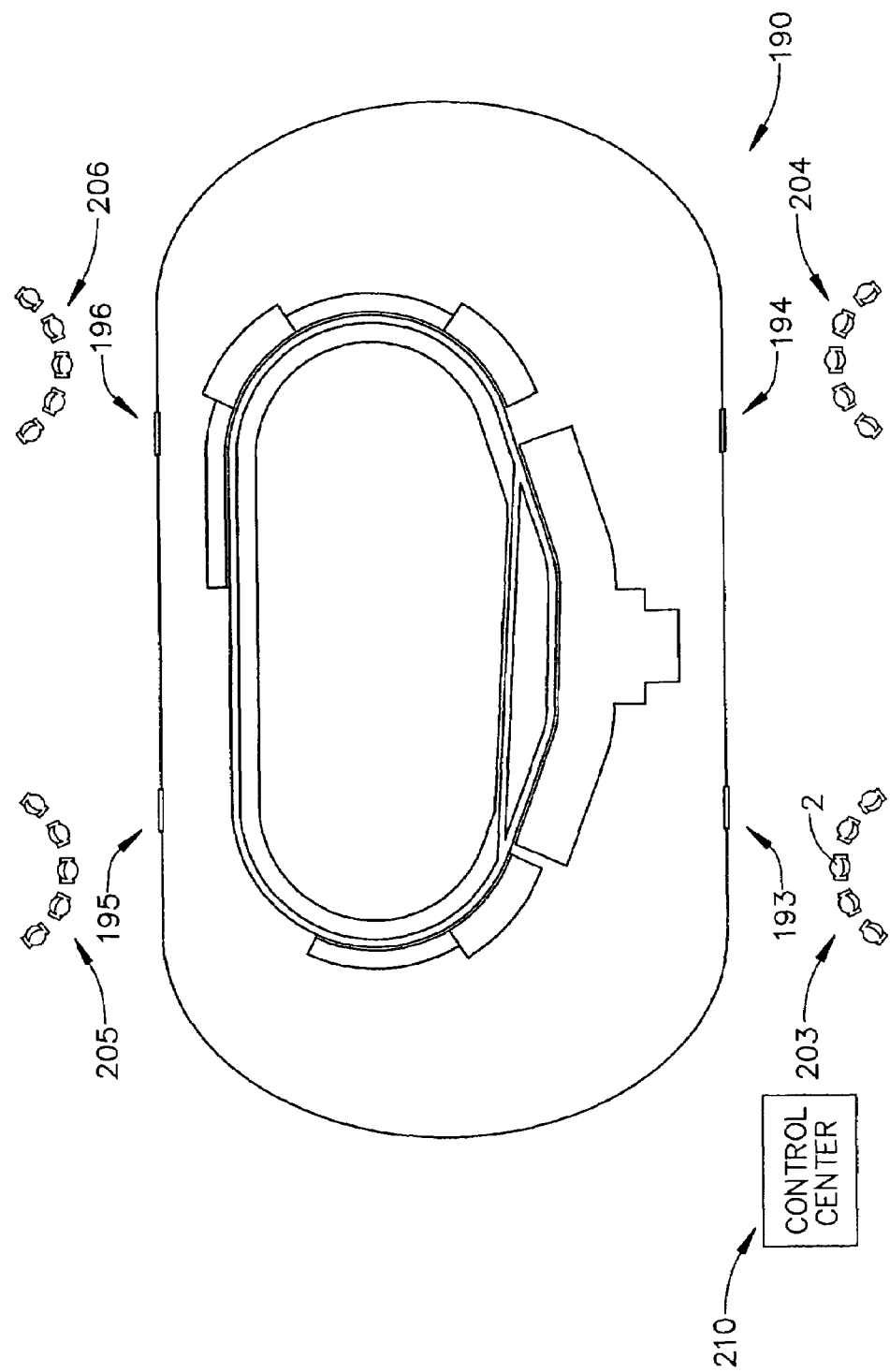
FIG. 5 is an aerial view of a venue having multiple access points, with clusters of screening centers located away from each access point in accordance with the present invention.

For use in connection with further describing the invention, FIG. 5 depicts the security and screening system of the present invention in connection with a venue 190, depicted as a car race track having multiple access points 193-196. As shown, arranged a requisite distance from each access point 193-196 is a screening center cluster such as indicated at 203 and 204 in connection with access points 193 and 194 respectively. Screening center clusters 203 and 204 include a plurality of screening centers 2 that screen individuals or subjects prior to entering venue 190 through access points 193-196. The number and location of clusters 203 and 204 are designed to enable a high throughput of subjects in order to prevent any significant delays in entering venue 190. In further accordance with the preferred form of the invention, each screening center 2 and each screening center cluster 203, 204 is fully integrated and connected to a central control 210, which could be located inside, outside or remote from venue 190, that enables security personnel to monitor screening processes, initiate security procedures, establish control updates and provide other support functions as needed while screening subjects looking to enter venue 190.

Figure 6:
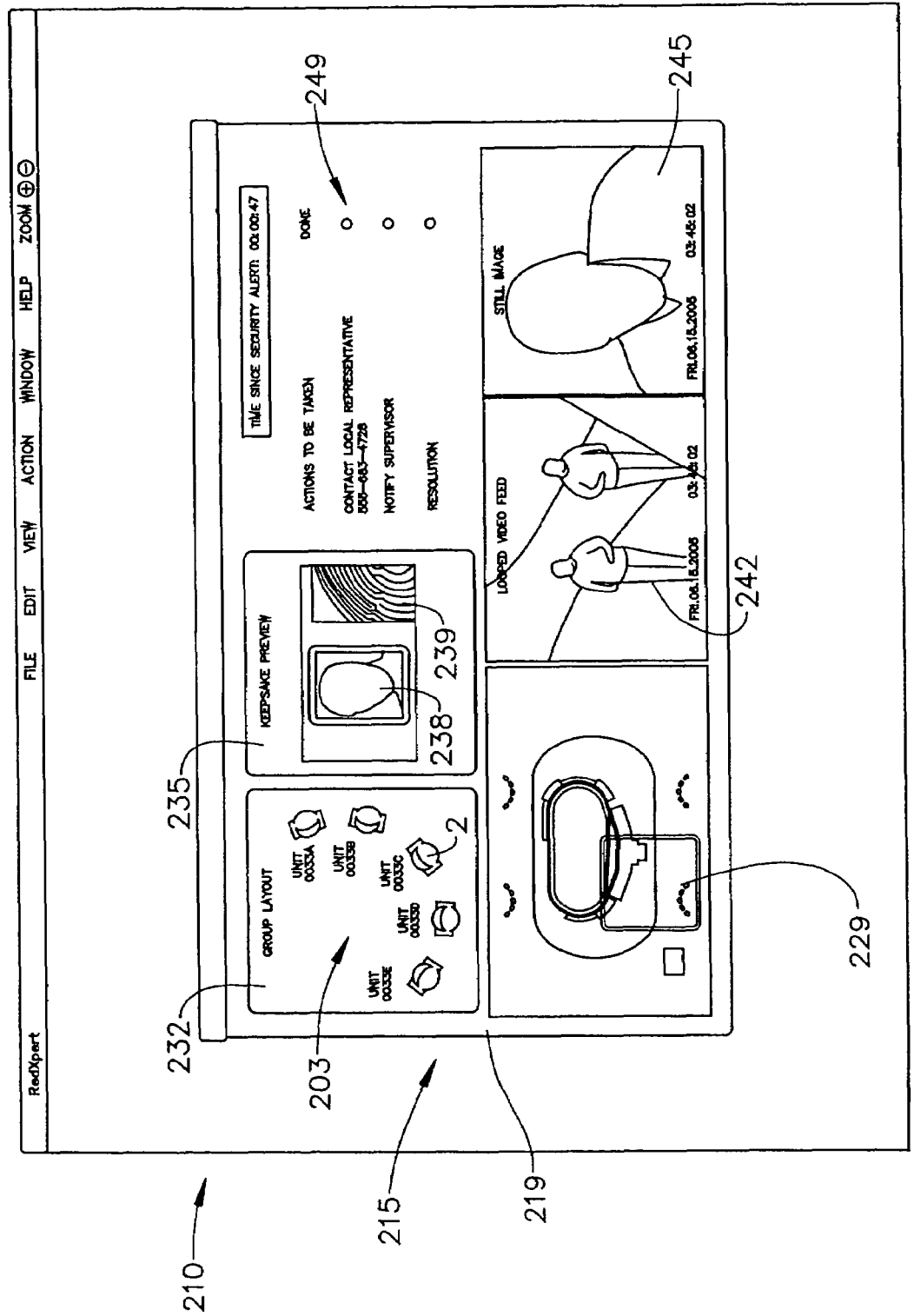
FIG. 6 illustrates a central control display including information obtained from one of the screening centers.

The overall manner in which the screening command and control receives, processes and responds to pertinent information can certainly vary. FIG. 6 illustrates one preferred command and control arrangement wherein central control 210 includes a main control display 215 presented following a positive test for an explosive residue at a screening center 2 which is part of cluster 203. As shown, main control display 215 presents a screen snapshot 219 having a location screen portion 229 that identifies a particular venue and/or portion of a venue from which the positive test was received and a cluster screen portion 232 that indicates a particular screening center 2 of the cluster 203 from which the positive test was received. Also shown is a keepsake view portion 235 including a photo portion 238 having a snapshot of the subject which tested positive, as well as a portion 239 of a sample image obtained during the requisite screening process, for further analysis. Screen 219 further includes a video screen portion 242 that presents a looped video, with or without audio, feed of the subject immediately before, during and after screening, as well as a close-up screen 245 that represents a still image, close-up photograph of a subject. Therefore, snapshot screen 219 provides security personnel with a host of location and subject information that can be used to access and respond to the potential threat. The system is shown to be on alert and pre-programmed alert actions to be taken are shown by alert status information indicated at 249. The alert status information preferably provides security personnel with a list of actions to be taken in connection with the security alert, while also keeping track of what actions have been completed and a time since the security alert occurred. In accordance with a preferred form of the invention, various predetermined standard responses or actions are automatically established as standard operating procedure upon receipt of a positive threat test result. However, the particular response employed is preferably randomized to counter the possibility of a group of threat potential individuals predicting future responses.

FIG. 7 presents an alert level screen 260, also preferably provided in connection with main control 210, which enables security personnel to view, monitor and update threat alert levels associated with various portions of venue 190. Furthermore, as shown in FIG. 8, main control 210 preferably includes an audit screen 270 that enables security personnel to ensure implementation of various security procedures, log alert status information occurring at various screening centers 2, implement a test alert and view the response of security personnel to actual and test scenarios.

With this overall construction, it should be readily apparent that the security screening and support system constructed in accordance with the present invention provides a high throughput, interactive system for screening unknowing subjects entering a venue for exposure to explosives. The screening system provides each test subject with a keepsake which represents a piece of memorabilia in some form or fashion, is required for entry into the venue, and provides an indication of the results of the explosive test. Moreover, the system not only screens for potential security threats, but presents demographic analysis to enable targeted advertising to be presented to the subjects which can help a business offset any costs associated with installation and maintenance of the overall system. By fully integrating the screening centers at a central control, security personnel can view, monitor, respond and analyze threat situations to ensure an efficient and coordinated response to any security alerts that may occur, while also permitting training and readiness assessment.

Although described with reference to a preferred embodiment of the invention, it should be readily understood that various changes and/or modifications can be made to the invention without departing from the spirit thereof. For instance, while being described in connection with a single venue, e.g., a race track, the present invention may be incorporated into multiple venues or venues having multiple discreet areas or sections in order to ensure the safety of workers, visitors and the like. In addition, the invention can be employed in connection with various types of threats so as to be not limited to explosive detection or the specific analyzing system described. To this end, the type of sample collector, i.e. threat sensor arrangement, can be based on direct physical contact with the subject or passive in nature, such as would be the case using, for example, a radiation detector or a millimeter wave sensor. Furthermore, although the embodiment described above outlined a security personnel review of each keepsake for a threat indicator, which could be either the presence or absence of some identifying mark on the keepsake, it should be realized that a keepsake need not be issued at all to any individual who tests positive. In such an arrangement, security personnel would be dispatched to the particular screening center in order to further evaluate the individual and the threat. To this end, the mere fact that an individual has a matching keepsake would justify entry into the venue, with the keepsake review being performed by either personnel or electronic machinery. In general, the invention is only intended to be limited by the scope of the following claims.

We claim:

1. A personnel security screening center comprising:
   a main housing;
   a threat screening system provided in the main housing, said threat screening system including:
      a sample collector for obtaining a threat sample, constituted by a trace residual sample, from a subject, said sample collector including a sample sheet;
      a sample analyzer operatively coupled to the sample collector, said sample analyzer screening the threat sample to determine whether the subject presents a potential threat; and
      a media feed device that transfers the sample sheet to the sample analyzer;
   a demographic screening system provided in the main housing, said demographic system including:
      a demographic collector for obtaining a demographic indicator from the subject; and
      a demographic analyzer operatively coupled to the demographic collector, said demographic analyzer determining a particular demographic of the subject based upon the demographic indicator; and
   an article issuing unit for issuing an article from the screening center after determining whether the subject presents a potential threat and determining the particular demographic of the subject, said article including a visual indication of the potential threat and advertising targeted to the particular demographic.

2. A personnel security screening center comprising:
   a main housing;
   a threat screening system provided in the main housing, said threat screening system including:
      a sample collector for obtaining a threat sample, constituted by a trace residual sample, from a subject, said sample collector including a sample sheet;
      a sample analyzer operatively coupled to the sample collector, said sample analyzer screening the threat sample to determine whether the subject presents a potential threat;
      a media feed device that transfers the sample sheet to the sample analyzer; and
      an article issuing unit for issuing an article to the subject from the screening center after determining whether the subject presents a potential threat, said article including a visual indication of the potential threat.

3. The personnel security screening center according to claim 2, wherein main housing defines a stand alone, user activated kiosk.

4. The personnel security screening center according to claim 2, wherein the article issued from the screening center constitutes a keepsake needed to enter a venue.

5. The personnel security screening center according to claim 4, wherein said keepsake includes a code indicative of the potential threat.

6. The personnel security screening center according to claim 5, wherein the code is constituted by an icon printed on the keepsake.

7. The personnel security screening center according to claim 2, further comprising: an adhesive provided on the sample sheet to both increase sample recovery and retain the trace residue sample.

8. The personnel security screening center according to claim 2, wherein the sample analyzer includes a UV light source that is directed onto the sample sheet.

9. A personnel security screening center comprising:
a main housing;
a threat screening system provided in the main housing, said threat screening system including:
   a sample collector for obtaining a threat sample from a subject; and
   a sample analyzer operatively coupled to the sample collector, said sample analyzer screening the threat sample to determine whether the subject presents a potential threat;
a demographic screening system provided in the main housing, said demographic system including:
   a demographic collector for obtaining a demographic indicator from the subject; and
   a demographic analyzer operatively coupled to the demographic collector, said demographic analyzer determining a particular demographic of the subject based upon the demographic indicator; and
advertising targeted to the particular demographic.

10. The personnel security screening center according to claim 9, wherein the demographic indicator is based on a hand feature of the subject.

11. The personnel security screening center according to claim 9, further comprising: a display provided on the main housing, said display presenting information to the subject.

12. The personnel security screening center according to claim 9, further comprising: a camera mounted to the main housing, said camera capturing a photograph of the subject.

13. The personnel security screening center according to claim 9, further comprising: an article issuing unit for issuing an article to the subject from the screening center, said article constituting a keepsake provided with the advertising.

14. A method of screening personnel for security risks prior to entry into a venue comprising:
performing a threat assessment including:
   directing a subject to a screening center;
   obtaining a threat sample, constituted by a trace residual sample on a sample sheet, from the subject;
   transferring the sample sheet to a sample analyzer with a media feed device; and
   analyzing the threat sample for at least one of a plurality of threat signatures to determine whether the subject presents a potential threat;
issuing an article to the subject after analyzing the threat sample, said article including a visual indicator of whether the threat sample contained the at least one of the plurality of threat signatures; and
examining the visual indicator to verify that the subject did not test positive prior to permitting the subject to enter the venue.

15. The method of claim 14, wherein the article takes the form of a keepsake needed to enter the venue.

16. The method of claim 14, further comprising:
performing a demographic assessment including:
   obtaining a demographic indicator from the subject; and
   analyzing the demographic indictor to determine a particular demographic of the subject; and
presenting advertising to the subject targeted to the particular demographic.

17. The method of claim 16, wherein the advertising is printed on the article.

18. The method of claim 14, further comprising:
capturing a photographic image of the subject; and
printing the photographic image on the article.

19. The personnel security screening center according to claim 9, wherein the threat sample constitutes a trace residual sample.

20. The personnel security screening center according to claim 19, wherein the sample collector includes a sample sheet and the personnel security screening center further comprises a media feed device that transfers the sample sheet to the sample analyzer.

* * * * *